United States Patent [19]

Hashimoto et al.

[11] Patent Number: 5,030,445

[45] Date of Patent: Jul. 9, 1991

[54] COSMETIC COMPOSITION

[75] Inventors: Shigeru Hashimoto, Oumihachiman; Takashi Umeno, Takatsuki; Midori Ukawa, Osaka; Norihiro Tanimoto, Okayama, all of Japan

[73] Assignees: Sunstar Kabushiki Kaisha; Teikoku Kako Co., Ltd., Osaka, Japan

[21] Appl. No.: 282,967

[22] Filed: Dec. 6, 1988

Related U.S. Application Data

[63] Continuation of Ser. No. 89,075, Aug. 25, 1987, abandoned.

[51] Int. Cl.$^5$ .................. A61K 7/021; A61K 7/027; A61K 7/42; A61K 7/48
[52] U.S. Cl. ........................... 424/59; 424/60; 424/63; 424/64; 424/69; 514/847; 514/873
[58] Field of Search ............ 424/59, 63, 69, 64

[56] References Cited

U.S. PATENT DOCUMENTS 4,603,047  7/1986  Watanabe et al. .............. 424/63

FOREIGN PATENT DOCUMENTS 2533497  2/1977  Fed. Rep. of Germany ........ 42/460

OTHER PUBLICATIONS

Macleod et al., Chem. Abs., 1971, vol. 75, p. 47399a.
Takehiko et al., Chem. Abs.; 1975, vol. 82, p. 144847x.

*Primary Examiner*—Dale R. Ore
*Attorney, Agent, or Firm*—Wegner, Cantor, Mueller & Player

[57] ABSTRACT

A cosmetic composition which comprises kaolin particles coated with titanium dioxide and one or more other conventional cosmetic ingredients.

3 Claims, No Drawings

COSMETIC COMPOSITION

This application is a continuation of U.S. application Ser. No. 089,075, filed Aug. 25, 1987, now abandoned.

FIELD OF THE INVENTION

The present invention relates to a cosmetic composition useful for preventing sunburn and suntan.

BACKGROUND OF THE INVENTION

Titanium dioxide powder has been widely used heretofore in various cosmetic compositions. Since finely granulated titanium dioxide particles having a maximum particle size of not more than $0.1\mu$, and an average particle size of 5 to 50 m$\mu$ show remarkable ultraviolet rays screening effect, recently, the use thereof in an anti-sunburn and anti-suntan cosmetic has been studied.

However, such finely granulated titanium dioxide particles have a large surface energy. Therefore, when a cosmetic is produced by using such titanium dioxide particles, it is difficult to uniformly disperse the particles in the cosmetic and the particles tend to form agglomerates during storage. Further, there are serious problems in the use of the finely granulated titanium dioxide particles as an ingredient for a cosmetic. For example, when it is formulated into a cake type foundation which is applied with water, the cosmetic is not uniformly applied to the skin upon use, which results in very bad finish.

OBJECTS OF THE INVENTION

Under these circumstances, the present inventors have studied intensively to obtain a cosmetic composition in which titanium dioxide having excellent ultraviolet rays screening effect are uniformly and stably dispersed. As the result, it has been found that the above problems in finely granulated titanium dioxide particles can be solved by using the titanium dioxide as a coating of kaolin particles.

SUMMARY OF THE INVENTION

According to the present invention, there is provided a cosmetic composition comprising titanium dioxide and other conventional cosmetic ingredients. The cosmetic composition of the present invention is characterized by using kaolin particles coated with titanium dioxide as said titanium dioxide.

In the cosmetic composition of the present invention, a larger amount of titanium dioxide can be formulated in comparison with a composition wherein titanium dioxide particles and kaolin particles are separately formulated. Therefore, the cosmetic composition of the present invention shows much higher ultraviolet rays screening effect and further it is homogeneous and stable. Furthermore, when the composition is applied to the skin, it gives very good finish and very good appearance as well as excellent anti-sunburn and anti-suntan effect.

DETAILED DESCRIPTION OF THE INVENTION

The kaolin particles coated with titanium dioxide used in the composition of the present invention can be prepared by adding a prescribed amount of kaolin particles having an average particle size of 0.5 to 30 m$\mu$ to an appropriate titanium salt such as titanium sulfate, titanium tetrachloride or the like, hydrolyzing the titanium salt in the presence of kaolin, and then, after filtration, washing and drying of the hydrolized mixture according to a conventional manner, calcining the mixture at about 300° C. to 90° C. for 10 to 180 minutes. For example, kaolin (135 g) having an average particle size of $2\mu$ is added to an aqueous solution of titanyl sulfate (1 liter) containing 15 g/liter of titanyl sulfate calculated as $TiO_2$ and the mixture is boiled with stirring for 2 hours. The product is filtered and washed with water. The resulting cake is separated and dried at 110° C. It is further calcined at about 800° C. for 30 minutes to obtain a desired kaolin particles coated with titanium dioxide.

In the kaolin particles coated with titanium dioxide thus obtained, surface of the matrix, the kaolin particle, is covered with fine particles of titanium dioxide.

Now, a cream containing the kaolin particles coated with titanium dioxide was prepared and its ultraviolet rays screening effect (SPF: Sun Protection Factor), transparency, blooming, and stability were compared with those of a cream prepared by the same manner except that a mixture of conventional finely granulated titanium dioxide particles having an average particle size of 8 m$\mu$ and kaolin was used instead of the kaolin particles. The results are shown in the following Table 1.

Further, according to the same manner as described above, SPF, dispersibility during preparation, and difference in a tint and finish upon use of a cake type foundation prepared by using the kaolin particles coated with titanium dioxide were evaluated. The results are shown in the following Table 2.

In the following description, all "%'s" are by weight unless otherwise stated.

Each cosmetic composition was obtained according to the following formulation and preparation.

| (a) Formulation of cream | |
|---|---|
| | Amount (%) |
| Ingredient A | |
| Solid paraffin | 5.0 |
| Beeswax | 4.0 |
| Microcrystalline wax | 4.0 |
| Vaseline | 7.0 |
| Squalane | 30.0 |
| Polyoxyethylene sorbitan monolaurate (20 EO) | 1.0 |
| Sorbitan sesquioleate | 4.0 |
| Ingredient B | |
| Distilled water | remainder |
| Ingredient C | |
| Kaolin coated with titanium dioxide [I] or a mixture of titanium dioxide and kaolin [II] (ratio of titanium dioxide in [I] or [II] is shown in Table 1) | see Table 1 |
| Talc | 5.0 |

The ingredients of C were homogeneously mixed and the ingredient of B is added to the mixture and thoroughly dispersed therein at 70° C. Separately, the ingredients of A were mixed and molten by heating at 70° C. and the above mixture was added thereto. The resulting mixture was emulsified with a homomixer. After emulsification, the mixture was cooled to 30° C. to obtain a cream.

| (b) Formulation of cake type foundation | |
|---|---|
| | Amount (%) |
| Ingredient A | |

-continued

| (b) Formulation of cake type foundation | |
|---|---|
| | Amount (%) |
| Kaolin coated with titanium dioxide [I] or a mixture or titanium dioxide and kaolin [II] (ratio of titanium dioxide in [I] or [II] is shown in Table 1) | see Table 1 |
| Talc | remainder |
| Red oxide of iron | 1.0 |
| Yellow oxide of iron | 2.5 |
| Black oxide of iron | 0.05 |
| Ingredient B | |
| Liquid paraffin | 8.5 |
| IPP | 1.0 |
| Sorbitan sesquioleate | 3.0 |
| Propylene glycol | 2.5 |
| Paraben | 0.2 |
| Ingredient C | |
| Perfume | 0.25 |

The above ingredients of A were stirred with Henschel mixer for 5 minutes. The ingredients of B which has been molten with heating at 70° C. in a separate vessel were added dropwise to the mixture of the ingredients of A with stirring. The ingredient of C was added to the resulting mixture and stirred for 1 minute. A prescribed amount of the mixture was filled in a metal pan to obtain a cake type foundation.

Evaluation of these compositions were carried out as follows.

(1) SPF

| Light source: | Toshiba FL20S.E-30 | 3 lamps |
|---|---|---|
| | central wavelength | 306 nm |
| | distance between light source and irradiated site | 60 cm |
| Irradiation site: | the back of Japanese adult men and women having fair skin and average skin, respectively | |
| Amount of application: | 0.2 g/100 cm$^2$ | |

Under the above conditions with varying irradiation time from 3 to 60 minutes at a constant light volume, according to the method for measuring SPF prescribed by FDA, the ratio of minimal erythema dose (MED) at a non-applied site and that of an applied site was calculated from the following formula:

$$SPF\ value = \frac{MED\ at\ the\ applied\ site}{MED\ at\ the\ non-applied\ site}$$

Propriety of the value determined was confirmed by the standard sunscreen (8% homosalat lotion) of FDA method 20 or more).

(2) Transparency

Ten panelists evaluated whether a white tint was observed or not when the creams were spread on the skin according to the following criteria.
A: All the ten panelists did not observe a white tint.
B: One to five panelists observed a white tint.
C: Six to nine panelists observed a white tint.

(3) Blooming

Ten panelists evaluated whether blooming (a blue tint) was observed or not when the creams were spread on the skin according to the following criteria.
A: All the ten panelists did not observe a blue tint.
B: One to five panelists observed a blue tint.
C: Six ti nine panelists observed a blue tint.

(4) Stability

After preparation of the creams, they were allowed to stand at 50° C. for one week and the existence of agglomerate (grain) was observed according to the following criteria.
A: No grain was observed.
B: Grain was slightly observed.
C: Grain was clearly observed.

(5) Dispersibility

After preparation of the cake type foundation by pressing, the existence of uneven lump (fine particles of titanium dioxide) was observed according to the following criteria.
A: No uneven lump was observed.
B: Uneven lump was slightly observed.
C: Uneven lump was clearly observed.

(6) Difference in tint

Ten panelists evaluated a tint of the cake type foundation itself in comparison with that after spread on the skin according to the following criteria.
A: Nine or ten panelists did not observed any difference in a tint.
B: Two to five panelists observed difference in a tint.
C: Six to eight panelists observed difference in a tint.

The difference in a tint is often observed in a cosmetic containing a conventional finely granulated titanium dioxide particles.

(7) Finish

The cake type foundation was applied on the skin with water. Whitening (such a phenomenon that powder applied was agglomerated and concentrated about the applied site to whiten) or unevenness of finish were evaluated according to the following criteria.
A: No whitening
B: Slight whitening (or powdery finish)
C: Whitening (or unevenness)

TABLE 1

| Runs | Amount of [I] or [II] | Titanium dioxide/[I] or [II] (%) | SPF value | Transparency | Blooming | Stability |
|---|---|---|---|---|---|---|
| Reference | [II] 4% | 10.0 | 1-2 | A | A | A |
| | | 30.0 | 2 | A | B | B |
| | | 50.0 | 3 | B | B | C |
| | | 70.0 | 3 | B | C | C |
| Present invention | [I] 4% | 10.0 | 1-2 | A | A | A |
| | | 30.0 | 2 | A | A | A |
| | | 50.0 | 3 | B | A | A |
| | | 70.0 | 3 | C | A | A |
| Reference | [II] 20% | 0 | 1 | A | A | A |

TABLE 1-continued

| Runs | Amount of [I] or [II] | Titanium dioxide/[I] or [II] (%) | SPF value | Transparency | Blooming | Stability |
|---|---|---|---|---|---|---|
| | | 0.5 | 1 | A | A | A |
| | | 1.0 | 1-2 | A | A | B |
| | | 5.0 | 2 | A | A | B |
| | | 10.0 | 3 | B | B | C |
| | | 30.0 | 8 | C | C | C |
| Present invention | [I] 20% | 0.5 | 1 | A | A | A |
| | | 1.0 | 1-2 | A | A | A |
| | | 5.0 | 3 | A | A | A |
| | | 10.0 | 4 | A | A | A |
| | | 30.0 | 8 | B | A | A |

TABLE 2

| Runs | Amount of [I] or [II] | Titanium dioxide/[I] or [II] (%) | SPF value | Dispersibility | Difference in tint | Finish |
|---|---|---|---|---|---|---|
| Reference | [II] 10% | 10.0 | 4 | A | B | A |
| | | 30.0 | 7 | B | B | A |
| | | 50.0 | 9 | B | C | B |
| | | 70.0 | 12 | C | C | C |
| Present invention | [I] 10% | 10.0 | 4 | A | A | A |
| | | 30.0 | 7 | A | A | A |
| | | 50.0 | 9 | A | A | A |
| | | 70.0 | 11 | A | A | B |
| Reference | [II] 50% | 0 | 3 | A | A | A |
| | | 0.5 | 3 | A | A | A |
| | | 1.0 | 4 | A | B | A |
| | | 5.0 | 6 | B | B | B |
| | | 10.0 | 9 | B | C | B |
| | | 30.0 | >15 | C | C | C |
| Present invention | [I] 50% | 0.5 | 3 | A | A | A |
| | | 1.0 | 4 | A | A | A |
| | | 5.0 | 7 | A | A | A |
| | | 10.0 | 10 | A | A | A |
| | | 30.0 | >15 | A | A | A |

As is seen from Tables 1 and 2, the kaolin particles coated with titanium dioxide can be formulated in a cosmetic composition in a wider range in comparison with a mere mixture of a conventional finely granulated titanium dioxide particles and kaolin. Further, the cosmetic composition containing the kaolin particles coated with titanium dioxide shows excellent ultraviolet rays screening effect and preferred cosmetic properties.

The amount of titanium dioxide to coat kaolin is preferably 1 to 50%. When the amount is less than 1%, ultraviolet rays screening effect can hardly be expected and, when the amount is more than 50%, cosmetic properties are impaired.

The kaolin particles coated with titanium dioxide can be formulated in a cosmetic composition of the present invention in an amount of not more than 90% by weight depending upon a type of cosmetics, usually, 90 to 1% by weight. Further, in the cosmetic composition of the present invention, a conventional finely granulated titanium dioxide particles can be formulated in an amount not more than 3% by weight.

The cosmetic composition of the present invention can be prepared in the form of, for example, a cake type or milky lotion type foundation, face powder, lipstick, milky lotion, cream and the like by incorporating the kaolin particles coated with titanium dioxide particles with other conventional cosmetic ingredients such as talc, iron oxides, liquid paraffin, solid paraffin, lanolin, sorbitan sesquioleate, beeswax, stearic acid, distilled water, sodium carboxymethyl cellulose, triethanol amine, propylene glicol and so on according to a conventional method. The other cosmetic ingredients are not limited to a specific one and they can be appropriately chosen according to a desired form and properties of the composition.

The following Examples further illustrate the present invention in detail but are not to be construed to limit the scope thereof.

EXAMPLE 1

A cake type foundation of the following formulation was prepared according to a conventional method.

| | Amount (%) |
|---|---|
| Ingredient A | |
| Kaolin particles coated with titanium dioxide (amount of coat: 10%) | 50.0 |
| Fine particulate titanium dioxide (average particle size 8 mµ) | 3.0 |
| Talc | 29.3 |
| Red oxide of iron | 0.6 |
| Yellow oxide of iron | 1.5 |
| Black oxide of iron | 0.15 |
| Ingredient B | |
| Liquid paraffin | 8.5 |
| Isopropyl palmitate | 1.0 |
| Sorbitan sesquioleate | 3.0 |
| Propylene glycol | 2.5 |
| Paraben | 0.2 |
| Ingredient C | |
| Perfume | 0.25 |

The ingredients of A were mixed with Henschel mixer for 5 minutes. To the mixture were added dropwise with stirring the ingredients of B previously molten by heating at 70° C. in a separate vessel. Then, the ingredient of C was added and the mixture was stirred for 1 minute. A prescribed amount of the resulting mixture was filled in a metal pan to obtain a cake type foundation.

In the preparation of the foundation, titanium dioxide was uniformly dispersed and, upon using, it could be uniformly applied on the skin to give very good finish.

EXAMPLE 2

A milky lotion type foundation of the following formulation was prepared according to a conventional method.

|  | Amount (%) |
| --- | --- |
| Ingredient A | |
| Liquid paraffin | 4.0 |
| Glyceryl monostearate | 2.0 |
| Stearic acid | 3.0 |
| Lanolin | 2.0 |
| Solid paraffin | 0.5 |
| Propylene glycol monostearate | 0.5 |
| Propyl p-hydroxybenzoate | 0.1 |
| Ingredient B | |
| Distilled water | 57.2 |
| Triethanol amine | 1.0 |
| Sodium carboxymethyl cellulose | 0.2 |
| Bentonite | 0.5 |
| Polyoxyethylene sorbitan monostearate | 1.5 |
| Propylene glycol | 7.5 |
| Ingredient C | |
| Kaolin coated with titanium dioxide (amount of coat: 30%) | 10.0 |
| Fine particulate titanium dioxide (average particle size: 8 mµ) | 2.0 |
| Talc | 5.0 |
| Red oxide of iron | 0.7 |
| Yellow oxide of iron | 2.0 |
| Black oxide of iron | 0.3 |

The ingredients of A and B were molten in separate vessels by heating at 80° C., respectively. The ingredients of B was added to the ingredients of A and the mixture was stirred for 10 minutes. The ingredients of C were added, and the mixture was stirred for 15 minutes and cooled to obtain a milky lotion type foundation.

In the preparation of the foundation, titanium dioxide was uniformly dispersed and, upon using, it could be uniformly applied on the skin to give very good finish.

EXAMPLE 3

A face powder of the following formulation was prepared according to a conventional method.

|  | Amount (%) |
| --- | --- |
| Ingredient A | |
| Kaolin coated with titanium dioxide (amount of coat: 1%) | 90.0 |
| Talc | 5.0 |
| Yellow oxide of iron | 1.5 |
| Red oxide of iron | 1.4 |
| Black oxide of iron | 0.1 |
| Ingredient B | |
| Squalane | 2.2 |
| Sorbitan sesquioleate | 0.5 |
| Ingredient C | |
| Perfume | 0.3 |

The ingredients of A were mixed with Henschel mixer for 5 minutes. The ingredients of B were uniformly molten in a separate vessel by heating at 70° C. and added dropwise to the ingredients of A with stirring. Further, the ingredient of C was added dropwise and the mixture was stirred for 1 minute. The mixture was pulverized with an atomizer to obtain a face powder.

In the preparation of the face powder, titanium dioxide was uniformly dispersed and, upon using, it could be uniformly applied on the skin to give very good finish.

EXAMPLE 4

A lipstick of the following formulation was prepared according to a conventional method.

|  | Amount (%) |
| --- | --- |
| Ingredient A | |
| Kaolin coated with titanium dioxide (amount of coat: 20%) | 5.0 |
| Mica powder | 5.0 |
| D & C Red No. 7 | 0.5 |
| D & C Red No. 9 | 0.5 |
| Ingredient B | |
| Candelilla wax | 7.0 |
| Solid paraffin | 7.0 |
| Beeswax | 5.0 |
| Carnauba wax | 5.0 |
| Castor oil | 44.8 |
| Isopropyl myristate | 10.0 |
| Ingredient C | |
| Perfume | 0.2 |

The ingredients of A and a part of castor oil were uniformly kneaded in a molar to obtain a pigment portion. The remaining ingredients of B were molten by heating. The pigment portion was added to the ingredients of B and uniformly dispersed with a homomixer. Further, the ingredient of C was added and uniformly dispersed. The mixture was cast in a mold and quickly cooled. The resulting solid was fixed in a container and framed.

In the preparation of the lipstick, titanium dioxide was uniformly dispersed and, upon using, it could be uniformly applied on the lip to give very good finish.

EXAMPLE 5

A milky lotion of the following formulation was prepared according to a conventional method.

|  | Amount (%) |
| --- | --- |
| Ingredient A | |
| Stearic acid | 3.0 |
| Cetyl alcohol | 1.5 |
| Vaseline | 5.0 |
| Liquid paraffin | 12.0 |
| Polyoxyethylene monooleate (10 EO) | 2.5 |
| Ingredient B | |
| Polyethylene glycol 1500 | 2.0 |
| Triethanol amine | 1.0 |
| Distilled water | 71.5 |
| Kaolin coated with titanium dioxide (amount of coat: 50%) | 1.0 |
| Ingredient C | |
| Perfume | 0.5 |

The ingredients of B were uniformly dispersed by heating at 70° C. The ingredients of A were molten by heating at 70° C. and added to the ingredients of B. The mixture was emulsified with a homomixer. After emulsification, the mixture was cooled with stirring to 30° C. to obtain a milky lotion.

In the preparation of the milky lotion, titanium dioxide was uniformly dispersed and was not agglomerated during storage. Upon using, it could be uniformly applied on the skin to give very good finish.

EXAMPLE 6

A cream of the following formulation was prepared according to a conventional method.

|  | Amount (%) |
|---|---|
| Ingredient A | |
| Solid paraffin | 5.0 |
| Beeswax | 4.0 |
| Microcrystalline wax | 4.0 |
| Vaseline | 7.0 |
| Squalane | 30.0 |
| Polyoxyethylene sorbitan monolaurate (20 EO) | 1.0 |
| Sorbitan sesquioleate | 4.0 |
| Ingredient B | |
| Distilled water | 20.0 |
| Ingredient C | |
| Kaolin coated with titanium dioxide (amount of coat: 5%) | 20.0 |
| Talc | 5.0 |

The ingredients of C were uniformly mixed and dispersed in the ingredient of B at 70° C. Separately, the ingredients of C were molten at 70° C. with heating and to this was added the above prepared mixture. The resulting mixture was emulsified with a homomixer. After emulsification, the mixture was cooled to 30° C.

In the preparation of the cream, titanium dioxide was uniformly dispersed and was not aggregated during storage. Upon using, it could be uniformly applied on the skin to give very good finish.

What is claimed is:

1. A composition comprising kaolin particles having a coating thereon consisting essentially of titanium dioxide, the amount of titanium dioxide coating the kaolin particles being 1 to 50% by weight based on the total weight of said kaolin particles coated with titanium dioxide.

2. A cosmetic composition according to claim 1, wherein the kaolin particles have an average particle size of 0.5 to 30 μm.

3. A cosmetic composition according to claim 1, wherein the kaolin particles coated with titanium dioxide is formulated in an amount of not more than 90% by weight based on the composition.

* * * * *